United States Patent
McInnes et al.

(10) Patent No.: US 10,067,131 B2
(45) Date of Patent: *Sep. 4, 2018

(54) FRAGMENT LIGATED INHIBITORS SELECTIVE FOR THE POLO BOX DOMAIN OF PLK1

(71) Applicant: University of South Carolina, Columbia, SC (US)

(72) Inventors: Campbell McInnes, Irmo, SC (US); Doaa Boshra Farag, Cairo (EG)

(73) Assignee: University of South Carolina, Columbia, SC (US)

( * ) Notice: Subject to any disclaimer, the term of this patent is extended or adjusted under 35 U.S.C. 154(b) by 353 days.

This patent is subject to a terminal disclaimer.

(21) Appl. No.: 14/710,962

(22) Filed: May 13, 2015

(65) Prior Publication Data

US 2015/0315555 A1     Nov. 5, 2015

Related U.S. Application Data

(63) Continuation of application No. 13/365,707, filed on Feb. 3, 2012, now Pat. No. 9,175,357.

(60) Provisional application No. 61/627,788, filed on Oct. 18, 2011, provisional application No. 61/462,577, filed on Feb. 4, 2011.

(51) Int. Cl.
| | |
|---|---|
| *C12N 9/16* | (2006.01) |
| *G01N 33/573* | (2006.01) |
| *A61K 47/48* | (2006.01) |
| *A61K 38/06* | (2006.01) |
| *A61K 38/08* | (2006.01) |
| *C12N 9/12* | (2006.01) |
| *C07K 5/083* | (2006.01) |
| *C07K 7/06* | (2006.01) |
| *G06F 19/18* | (2011.01) |

(52) U.S. Cl.
CPC .......... *G01N 33/573* (2013.01); *A61K 38/06* (2013.01); *A61K 38/08* (2013.01); *A61K 47/48023* (2013.01); *A61K 47/48038* (2013.01); *A61K 47/48061* (2013.01); *C07K 5/081* (2013.01); *C07K 7/06* (2013.01); *C12N 9/12* (2013.01); *C12N 9/16* (2013.01); *C12Y 207/11021* (2013.01); *G06F 19/18* (2013.01); *C07K 2317/34* (2013.01); *C12Y 301/03048* (2013.01); *G01N 2333/912* (2013.01); *G01N 2500/02* (2013.01)

(58) Field of Classification Search
None
See application file for complete search history.

(56) References Cited

U.S. PATENT DOCUMENTS

| | | |
|---|---|---|
| 7,449,544 B2 | 11/2008 | Zheleva et al. |
| 8,566,072 B2 | 10/2013 | McInnes et al. |
| 9,175,357 B2 * | 11/2015 | McInnes ................ C12N 9/12 |
| 2003/0129656 A1 | 7/2003 | Park et al. |
| 2003/0171904 A1 | 9/2003 | Lewis et al. |
| 2003/0187220 A1 | 10/2003 | Park et al. |
| 2003/0225527 A1 | 12/2003 | Antonysamy et al. |
| 2004/0229290 A1 | 11/2004 | Hellinga et al. |
| 2005/0196808 A1 | 9/2005 | Yaffe et al. |

FOREIGN PATENT DOCUMENTS

WO    WO2007140233 A1 * 12/2007 ........... C07C 225/20

OTHER PUBLICATIONS

Elia et al. Proteomic screen finds pSer/pThr-binding domain localizing Plk1 to mitotic substrates. Science. Feb. 21, 2003;299(5610):1228-31.*

Huggins et al. Computational analysis of phosphopeptide binding to the polo-box domain of the mitotic kinase PLK1 using molecular dynamics simulation. PLoS Comput Biol. Aug. 12, 2010;6(8). pii: e1000880.*

Rich et al. Preparation of a new o-nitrobenzyl resin for solid-phase synthesis of tert-butyloxycarbonyl-protected peptide acids. J Am Chem Soc. Mar. 19, 1975;97(6):1575-9.*

Peptide Design. https://www.thermofisher.com/us/en/home/life-science/protein-biology/protein-biology-learning-center/protein-biology-resource-library/pierce-protein-methods/peptide-design.html downloaded Sep. 16, 2017.*

Reindl et al. Inhibition of Polo-like Kinase 1 by Blocking Polo-Box Domain-Dependent Protein-Protein Interactions. Chemistry & Biology 15, 459-466, May 2008. (Year: 2008).*

(Continued)

*Primary Examiner* — Marcela M Cordero Garcia
*Assistant Examiner* — Jia-Hai Lee
(74) *Attorney, Agent, or Firm* — Dority & Manning, P.A.

(57) ABSTRACT

Methods for developing non-peptidic inhibitors that target the polo-box domain of PLK1 proteins are described. Methods include developing structure activity relationships for peptidic inhibitors followed by development of non-peptide fragment alternatives for portions of the peptide inhibitors. The non-peptide fragment can provide similar structure activity relationship as the replaced peptide. Fragment alternatives to key binding determinants are identified in an iterative computational and synthetic process facilitated through understanding of the peptide structure-activity relationships. The approach is informed by peptide structure-activity data obtained through synthesis and testing of truncated and mutated analogs of known PBD binding motifs.

5 Claims, 3 Drawing Sheets

Specification includes a Sequence Listing.

(56) References Cited

OTHER PUBLICATIONS

Yun et al. Structural and functional analyses of minimal phosphopeptides targeting the polo-box domain of polo-like kinase 1. Nat Struct Mol Biol. Aug. 2009;16(8):876-82. (Year: 2009).*
D.I. Zheleva et al. "Highly potent p21 WAF1-derived peptide inhibitors of CDK-mediated pRb phosphorylation: Delineation and structural insight into their interactions with cyclin A" *J. Peptide Res.*, 2002, 60, 257-270.
Sintchak, Michael D. and Nimmesgem, Elmar; "The structure of inosine 5'monophosphate dehydrogenase and the design of novel inhibitors." Immunopharmacology (2000) 47 p. 163-184).
Milik, Mariusz et al; "Algorithm for rapid reconstruction of protein backbone from alpha carbon coordinates." J. Comp. Chem. (1997) 18(1) p. 80-85.
Andrews, Martin J. I. et al; "Replace: a strategy for iterative design binding grove inhibitors." Chembiochem (2006) 7 p. 1909-1915.
Liu, Shu et al; "Structural and functional analysis of cyclin d1 reveals p27 and substrate inhibitor binding requirements." ACS Chem. Biol. (2010) 5(12) p. 1169-1183.
Cho et al. Journal of Computational Chemistry, vol. 26, Issue 1, pp. 48-71, 2005
Sundaramoorthi, Structure-Based Design of Novel Nonpeptide Inhibitors of the Src SH2 Domain: Phosphotyrosine Mimetics Exploiting Multifunctional Group Replacement Chemistry, Bioploymers (Pept Sci) 71 : 717-729, 2003.

* cited by examiner

FRAGMENT LIGATED INHIBITORS SELECTIVE FOR THE POLO BOX DOMAIN OF PLK1

CROSS REFERENCE TO RELATED APPLICATION

This application is a continuing application claiming filing priority to U.S. patent application Ser. No. 13/365,707 having a filing date of Feb. 3, 2012, which claims filing benefit of U.S. Provisional Patent Application Ser. No. 61/462,577 having a filing date of Feb. 4, 2011 and U.S. Provisional Patent Application Ser. No. 61/627,788 having a filing date of Oct. 18, 2011, all of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Apr. 5, 2018, is named USC-301-CON (881) SL.txt and is 7,000 bytes in size.

BACKGROUND

The family of polo-like kinase (PLK) proteins are central players in regulating are central players in regulating entry into and progression through mitosis. The four known human PLKs have non-redundant and non-overlapping functions. A significant body of literature has validated PLKs as anti-tumor drug targets and suggested that profound anti-proliferative activity is achieved through selective inhibition of PLK1 functions. Over-expression of PLK1 is frequently observed and PLK1 expression is a prognostic indicator for outcome of patients suffering from various tumors. For example, more than half of prostate cancers over-express PLK1 and this expression is positively correlated with tumor grade. PLK1 is also extensively over-expressed in colorectal cancer and recently has been demonstrated to be a potential therapeutic target in colorectal cancer cell lines with inactivated p53. Moreover, it has been reported that p53 transcriptionally regulates PLK1 expression, providing more direct evidence that PLK1 is oncogenic when p53 is mutated. Thus, there is a strong rationale for pursuing PLK1 as an anti-tumor drug target. Indeed, the therapeutic rationale for PLK inhibition has been validated through studies with PLK1-specific antisense oligonucleotides and shown to profoundly induce growth inhibition in cancer cells both in vitro and in vivo.

Numerous inhibitors of ATP binding to the catalytic site in the N-terminal region of the PLKs have been identified with some entering clinical trials after showing significant anti-tumor activity in preclinical models. At least two compounds have been evaluated in phase I clinical trials. Published results from these two compounds suggest acceptable toxicity profiles thus warranting further investigation in phase II trials.

The human PLK family has four members that play a key role in mitotic progression and DNA integrity. Of the four family members, PLK1 is the best-characterized. A significant potential drawback of compounds that target the PLK1 ATP cleft is that other members of the PLK family are likewise targeted by the compounds. For instance, at least 3 of the 4 known members of the mammalian PLKs are inhibited by BI2536, the most advanced PLK inhibitor found to date. Contrary to the role of PLK1 in cell proliferation and tumorigenesis, its two most closely related family members, PLK2 and PLK3, appear to play a role in check-point mediated cell-cycle arrest. Since PLK3 has been reported to have opposing functions to PLK1 (collective evidence indicates that PLK3 acts as a tumor suppressor), inhibition of this kinase may lead to diminution of the anti-tumor effect mediated by blocking PLK1 activity. For instance, it has been shown that mice deficient in PLK3 were susceptible to tumors in various organs and that tumor suppressor activity could be directly attributed to the catalytic domain. It has also been demonstrated that PLK3 positively regulates the PTEN tumor suppressor. These issues were revealed subsequent to the initial clinical development of ATP-competitive PLK inhibitors and strongly suggest that inhibiting PLK3 would not be a desirable feature of a clinical candidate. In addition, ATP competitive inhibitors will only block the enzymatic functions of PLK1 and will not necessarily have an effect against other critical functions in mitosis.

The two domains found in the human PLK1 are the highly-conserved N— are the highly-conserved N-terminal kinase domain and the unique polo box domain (PBD) containing two polo boxes. The PBD involves phosphopeptide binding, which helps regulate substrate binding at the kinase catalytic domain. Previous studies with peptides provide evidence that the substrate and sub-cellular targeting binding site in the PBD forms a compact and druggable interface amenable to inhibitor development. Although high-throughput screening approaches have identified small molecule inhibitors of the PBD-peptide interaction, these either are weakly binding or non-drug-like in nature. In addition, these inhibitors display a contrasting phenotype to PLK1 knockdown and to cellular treatment with inhibitors of catalytic activity. Peptide inhibitors have also been found that can target the PBD domain and discriminate between the PLK family members. Unfortunately, however, while peptides make excellent inhibitors, they generally exhibit poor pharmacokinetic properties and as such have not proven useful in clinical settings.

What are needed in the art are alternative approaches to develop potent and highly selective PLK1 inhibitors and PLK1 inhibitors developed by such methods. A PLK1 selective inhibitor could beneficially avoid inhibition of the tumor suppressor activity of PLK2 and PLK3. In addition, a PLK1 inhibitor that targets the distinctive binding site on the PBD could be used to generate novel anticancer therapeutics that are both discriminatory to PLK1 and less toxic to normal cells.

SUMMARY

According to one embodiment, disclosed is a method for developing a fragment ligated inhibitor that is selective for the PBD of the PLK1 protein. For instance, a method can include replacing one or more amino acid residues of a peptide PBD selective PLK1 inhibitor with a non-peptide fragment. More specifically, the amino acid residue(s) that are replaced with the non-peptide fragment can include a terminal amino acid residue of the peptide PBD selective PLK1 inhibitor.

Also disclosed are fragment ligated inhibitors that can be developed according to the disclosed methods. For example, a fragment ligated inhibitor can include a non-peptide fragment that is ligated to a terminus of the inhibitor, wherein the non-peptide fragment mimics the structure activity relationship of a peptide fragment of an inhibitor that is selective for the PBD of a PLK1 protein.

BRIEF DESCRIPTION OF THE FIGURES

FIG. 4 discloses SEQ ID NOS 5, 15 and 13, respectively, in order of appearance.

DETAILED DESCRIPTION

Figure 1A:
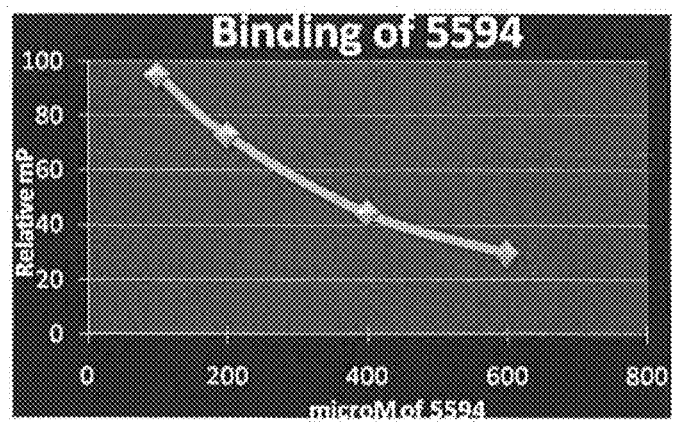
FIGS. 1A and 1B present binding curves for fragment ligated inhibitors formed as described herein.

The following description and other modifications and variations to the present invention may be practiced by those of ordinary skill in the art, without departing from the spirit and scope of the present invention. In addition, it should be understood that aspects of the various embodiments may be interchanged both in whole and in part. Furthermore, those of ordinary skill in the art will appreciate that the following description is by way of example only, and is not intended to limit the invention.

In general, disclosed herein are methods for forming fragment ligated inhibitors that are specific for the PBD domain of the PLK1 protein. More specifically, the fragment ligated inhibitors are formed by replacing one or more peptide segments of a known peptide inhibitor with non-peptide fragment(s). Each non-peptide fragment is developed so as to substantially maintain and mimic the structure activity relationship of the replaced peptide segment of the peptide inhibitor. As such, fragment ligated inhibitors formed according to the disclosed methods can be better suited for use in clinical settings as compared to peptide inhibitors, which generally exhibit poor pharmacokinetic properties. For instance, the non-peptide fragment ligated to the terminal portion of a peptide can protect the core amino acid residues from proteolytic degradation thereby improving half life with in the cell. In one embodiment, the process can be iterated, replacing additional peptide fragments of the original peptide PLK1 inhibitor to form a completely non-peptide inhibitor.

A peptide structure activity relationship describes key determinants and novel information useful for drug design. Fragment ligated inhibitors generated according to disclosed methods can exhibit comparable affinity to peptidic PBD inhibitors and can possess anti-proliferative phenotypes in cells consistent with the observed decrease in PLK1 centrosomal localization. The fragment ligated inhibitors can demonstrate evidence of enhanced PLK1 inhibition in cells relative to peptides and can induce monopolar and multipolar spindles, in contrast to previously reported small molecule PBD inhibitors that display phenotypes only partially representative of PLK1 knockdown. The fragment ligated inhibitors can show promise as isotype, kinase selective, non-ATP competitive inhibitors and provide impetus for the development of PLK1 selective anti-tumor therapeutics.

According to the present disclosure, peptide inhibitors that can discriminate between PLK family members and can target the PBD of PLK1 provide the structural basis for the development of the fragment ligated inhibitors. Herein, iterative development of protein-protein interaction inhibitors has been applied to develop fragment alternatives for portions of previously known peptide inhibitors. For instance, in one embodiment, a method can include replacement of the N-terminal hydrophobic motif in a CDC25c PBD substrate peptide with a non-peptide fragment that can provide similar structure activity relationships as the replaced peptide. In this approach, fragment alternatives to key binding determinants are identified in an iterative computational and synthetic process facilitated through understanding of the peptide structure activity relationships. This approach is informed by peptide structure activity data obtained through synthesis and testing of truncated and mutated analogs of known PBD binding motifs.

Using transfected fragment ligated inhibitors, a workflow for phenotypic and PLK1 specific cellular effects has been established using anti-proliferative, flow cytometry and subcellular localization assays. Beneficially, the fragment ligated inhibitors can replicate a PLK1 phenotype, in contrast to the partial phenotype obtained with PBD dominant negative and small molecule inhibitors utilized in the past. Thus, it is believed that inhibitors formed as described herein can inhibit both subcellular localization and substrate phosphorylation.

Peptide inhibitors that can be utilized as the basis for development of the fragment ligated inhibitors can include any peptide inhibitor capable of selectively inhibiting PLK1. For instance, the basis peptide inhibitor can include both native peptides and variants thereof. In one embodiment, the peptide inhibitor can include a core group of amino acid residues (e.g., about three or more amino acid residues) that will also form a core peptide of the fragment ligated inhibitor. For example, a core peptide of amino acid residues that is present in the peptide inhibitor that is utilized as a basis for formation of the fragment ligated inhibitor can correlate to a core peptide of the same amino acid residues in the formed fragment ligated inhibitor. In one embodiment, the core peptide group can include an S-[pT/pS]-[P/X] (SEQ ID NO: 1) motif, which binds the PBD of PLK1 along the positively charged cleft between the two polo boxes. For example, the core peptide can include an S[pT]P (SEQ ID NO: 2) motif. This is not a requirement, however, and in another embodiment, the complete peptide structure of the peptide inhibitor that is utilized as a basis can be replaced, one fragment at a time, to form a nonpeptide fragment ligated inhibitor.

By way of example, peptide inhibitors utilized as a basis for development of the fragment ligated inhibitors can include the native CDC25c PBD binding sequence or variants thereof, those from nonnative ligands discovered using a phosphopeptide screening approach as described by Elia, et al. (see, e.g., Science, 2003. 299 (5610:p. 1228-1231; Cell, 2003. 115(1):p. 83-95), and the native PBIP PBD binding sequence also known as CENP-Q or variants thereof.

In one embodiment, minimized PBD binding sequences of selective peptides, for example 5 and 6-mer peptides as have been identified through truncation and found to have an increased level of selectivity for PLK1 over the longer sequences previously studied can be used to develop the fragment ligated inhibitors. For instance, the PBIP recognition motif that has been identified as PLHS(pT) (SEQ ID NO: 3), a peptide with a $K_d$ of 0.45 μM can be used. In another embodiment, the LHS(pT)AI (SEQ ID NO: 4) sequence of similar potency can be used, which has a Kd of 0.25 μM. In yet another embodiment, the CDC25c PBD binding sequence LLCS[pT]PNGL (SEQ ID NO: 5) can be utilized to develop the fragment ligated inhibitors.

In development of the fragment ligated inhibitors, the peptide inhibitor used as a basis is first examined to determine the structure activity relationship of the peptide inhibitor, and in one embodiment of fragments (e.g., 2, 3, or 4 amino acid residues) of the peptide inhibitor. Any testing methodology as is known in the art can be utilized in determination of the structure activity relationship of the peptide inhibitor utilized as a basis. For instance, analog formation, computational design, comparative binding assays, and the like can be utilized according to known practice to determine the structure activity relationships of the peptide inhibitor, and particularly in determining the structure activity relationship of one or more of the terminal amino acid residues and/or the core amino acid residues of the peptide inhibitor that will be replaced by a non-peptide fragment in formation of a fragment ligated inhibitor.

Following determination of the structure activity relationship of specific peptides of the peptidic inhibitor used as a basis, low molecular weight fragments can be computationally docked into the volume of a binding site known to interact with key peptidic determinants of the protein-protein interaction, while still preserving the context of the peptide core structure in one embodiment. For instance, through use of the structure activity data generated from analysis of binding of synthetic peptides to the PBD, fragment alternatives can be identified to replace one or more terminal amino acid residues, e.g., one, two, three, four, or more terminal amino acid residues of the peptide inhibitor on one or both of the N-terminal and the C-terminal of the peptide inhibitor used as a basis. For example, a fragment alternative can be identified for the N-terminal tripeptide LLC (SEQ ID NO: 17) of the CDC25c PBD binding sequence LLCS[pT]PNGL (SEQ ID NO: 5). Each potential non-peptide fragment can be scored through energetic and geometric evaluation of docked poses in the context of the bound core peptide according to known methodology.

The docked fragments can have any chemical structure that can mimic the docking of the amino acid residue(s) to be replaced that also includes the potential for incorporation of appropriate functionality to allow ligation onto a truncated peptide (e.g., the core peptide minus the amino acids to be replaced). For example, a fragment can include or be capable of functionalization to include a carboxylate group that can allow ligation to the truncated peptide.

Any suitable docking methodology can be utilized to examine a potential non-peptide fragment for suitability as a replacement for one or more peptides at a terminus of the peptide inhibitor used as a basis. By way of example, LigandFit (Accelrys, San Diego, USA) can be utilized for determining fit of a potential fragment into the volume of the peptide binding groove occupied by the LLC (SEQ ID NO: 17) tripeptide at the N-terminus of the CDC25c binding sequence LLCS[pT]PNGL (SEQ ID NO: 5). Any algorithm as is known in the art may be utilized for examining potential non-peptide fragments including, without limitation, LigandFit, Dock, FlexX, FlexE, Slide, Fred, Gold, Glide, AutoDock, LigandFit, ICM, QXP, Amber, CHARMM, SCORE, VALIDATE, Chemscore, Ludi, PLP, PMF, Bleep, SmoG, ZAP, VIDA, GRID, MCSS, Superstar and ROCS.

According to one embodiment, docking modeling can be carried out using LigandFit. The non-peptide fragment can be docked to the N-terminus of the core-peptide structure using interaction filters, to allow for amide bond formation during synthesis. Site points can be generated using a grid resolution of about 0.5 Å with a radius of about 2.5 Å for the ligand atoms. The Dreiding force field and Gasteiger partial charges can be employed for ligand fitting with a non-bonded cutoff of about 10 Å and distance dependent dielectric constant. Prior to synthesis, a compound can be further modeled by formation of the fragment-peptide structure and energy minimization performed after the protein's bonds are constrained.

In one embodiment, non-peptide fragments can include a naphthoic acid derivative or a benzoic acid derivative. By way of example, derivatives can include substituted or unsubstituted groups including, without limitation, branched or straight chained alkyl groups, cycloalkyl groups, heterocycloalkyl groups, aryl groups, heteroaryl groups, phosphate groups, sulphate and/or sulfhydryl groups, halogens, and so forth.

The chosen fragment can be ligated to one or more core amino acid residues of the peptide inhibitor or to a previously formed non-peptide fragment of the fragment ligated inhibitor, for instance via a carboxylate group and formation of an amide bond, to form the final fragment ligated inhibitor. The number of amino acid residues replaced at the terminus of a peptide inhibitor can vary. For instance a tripeptide as described above may be replaced. Alternatively, a single amino acid residue, two amino acid residues, or more may be replaced by a non-peptide fragment that can mimic the function of the replaced residues.

The fragment modifications to peptide inhibitors such as the CDC25c PBD binding sequence can result in non-ATP competitive fragment ligated inhibitors having ability to block PLK1 cellular functions, which can induce mitotic defects and trigger apoptosis. The fragment ligated inhibitors can also possess enhanced cellular stability and therefore potency relative to peptidic PBD inhibitors, even if they exhibit similar or lower in vitro binding activity. The fragment ligated inhibitors can also recapitulate a PLK1 phenotype not observed with small molecule PBD binding compounds. Taken together, such benefits of the disclosed approach to generate non-ATP competitive anti-tumor therapeutics can be of great benefit in the art.

The present disclosure may be better understood with reference to the Examples provided below.

Experimental Procedures

Molecular Docking

Docking was performed using LigandFit (Accelrys, San Diego, USA). Non-peptide fragment groups were docked to the N-terminus of the core-peptide structure using interaction filters, to allow for amide bond formation during synthesis. Site points were generated using a grid resolution of 0.5 Å with a radius of 2.5 Å for the ligand atoms. The Dreiding forcefield and Gasteiger partial charges were employed for ligand fitting with a non-bonded cutoff of 10 Å and distance dependent dielectric constant. Prior to synthesis, compound are further modeled by formation of the fragment-peptide structure and energy minimization performed after the protein's bonds are constrained.

Peptide & Fragment Ligated Inhibitor Synthesis

Peptides and Phospho-Peptides were synthesized and purified using standard Fmoc chemistry by GenScript (Piscataway, N.J.). Coupling of a tracer peptide to fluorescein isothiocyanate for a fluorescent polarization (FP) assay was also done by GenScript. Unless stated otherwise, all peptides were synthesized with an N-terminal amino group and a C-terminal carboxyl group. High-performance liquid chromatography (HPLC) and mass spectrometry (MS) techniques were used to confirm the purity and structure of each peptide.

Fluorescent Polarization Binding Assay

The buffer composition was 50 mM Tris, 200 mM NaCl, 2.0 mM DTT, and 0.005% Tween 20 (pH 8.0). Fragment ligated inhibitors and comparison peptides to be tested in the binding assay were dissolved in dimethyl sulfoxide (DMSO) to a concentration of 10 mM, compounds were utilized in a range of concentrations from 10 nM to 600 μM. The PLK1 PBD protein (residues 367-603) was obtained from BPS Bioscience Inc. (San Diego, Calif.) and 250 ng was used per sample. The fluorescein-tracer phospho-peptide was used at a final concentration of 100 nM. Each sample was prepared in triplicate in a black 96-well plate (Greiner, Monroe, N.C.). Reactants were added to the plate in darkened conditions to minimize exposure to light. Incubation was carried out at room temperature for 45 minutes. Fluorescence was measured using a DTX 880 Multimode detector plate reader (Beckman Coulter, Brea, Calif.) and Multimode Analysis software (Beckman Coulter). The polarization values in millipolarization (mP) units were measured at an excitation wavelength of 488 nm and an emission wavelength of 535 nm with the following equation:

$$p = \frac{I_\parallel - GI_\perp}{I_\parallel + GI_\perp}$$

Where $I_\parallel$ is the intensity with polarizers parallel and $I_\perp$ signifies the intensity with the polarizers perpendicular. G represents the instrumental error.

Cell Culture

HeLa cervical cancer cells were obtained from ATCC (Manassas, Va.). Histone 2B GFP-labeled HeLa cells (HeLa-H2B-GFP) were kindly provided by Dr. Geoffrey Wahl (Gene Expression Laboratory, Salk Institute). Cells were maintained in DMEM (Invitrogen, Carlsebad, Calif.) supplemented with 10% Nu-serum (BD Bioscience, Franklin Lakes, N.J.) and 1% penicillin/streptomycin (Invitrogen) in a humidified incubator in 95% air and 5% $CO_2$ at 37° C. Cells were plated at 20-30% confluence at least 24 h prior to treatment.

Peptide Transfection

Peptides and fragment ligated inhibitory proteins were transfected into cells using a reagent known as QQ, which has been previously described by Dr. Jianjun Wang (Wayne State University). Polyethylenimine (PEI), N-(2,3-Dioleoyloxy-1-propyl)trimethylammonium methyl sulfate (DOTAP methosulfate), 1,2-Dioleoyl-sn-glycero-3-phosphoethanolamine (DOPE), DMSO, and MG132 were obtained from Sigma Aldrich (St Louis, Mo.). The following modifications were made to the protocol: a 10 mg/mL stock solution of P8 was made by diluting PEI (50 wt. % in $H_2O$) with 50 mM phosphate buffer and using 6 M HCl (Sigma Aldrich) to adjust the pH to 7.4. MG132 was resuspended in 0.1 M DMSO to make a 5 μg/mL stock solution of MG132. The final concentration of the components were 0.25 mg/mL and 5 ng/mL, respectively.

Immunofluorescence, PLK1 localization, and Aberrant Prometaphase/Metaphase Analysis HeLa-H2B-GFP cells were plated at a density of 10,000 cells per coverslip for 24 h prior to thymidine block. Cells were synchronized by a single thymidine block by exponentially growing cells treated with 2 mM thymidine (Sigma Aldrich) for 18 h and followed by two washes with PBS (Sigma Aldrich). Fresh growth medium was then added and the cells incubated at 37° C. with or without treatment. After the indicated treatment time, the coverslips were washed with PBS. The cells were fixed with 4% formaldehyde (ThermoFisher Scientific) and permeabilized with 0.2% Triton X-100. Fixed cells were incubated with PLK1 antibody (Cell Signaling Technology, Danvers, Mass.) overnight at 4° C. and Alexa Fluor 488-conjugated anti-rabbit secondary IgG (Molecular Probes) for 1 h at room temperature to visualize PLK1. The cells were mounted and the coverslips were examined with an Olympus microscope (IX81), using a 100× objective, and the images were captured using a Hamamatsu OrcaR2 camera. PLK1 localization was analyzed for cells in metaphase using MetaMorph software (Molecular Devices). Images were taken in z-stacks, overlayed and deconvoluted. A minimum of 20 centrosomes were analyzed per slide. Cells were considered to be in normal prometaphase and normal metaphase when they had two clearly defined and separated centrosomes while those marked as aberrant had either a single centrosome or multiple centrosomes. Metaphase cells with misaligned chromosomes were scored as aberrant.

Analysis of Apoptosis

At the indicated intervals, cells were collected by trypsinization, washed with PBS, fixed in 100% ethanol overnight, incubated with propidium iodine (50 ug/mL) and RNase A (0.5 mg) for a minimum of 30 min. Staining with FITC-Annexin V was carried out as described by the manufacturer (BD Biosciences). The samples were analyzed using a Beckman-Coulter FC 500 flow cytometer. Data were quantified using ModFit LT software version 3.1 (Verity Software House)

Statistical Analysis

Calculations of the mean, standard deviation, and standard error were performed using Microsoft Excel. Statistical analysis for comparison of each set of experimental means as well as statistical analysis of proportions was performed using Statistics 8 CS (StatSoft, Inc.).

Example 1

The analysis of the structure activity relationship and binding determinants of the phosphorylated sequence LLCS[pT]PNGL (SEQ ID NO: 5), the CDC25c PBD binding sequence, was carried out. The sequence LLCSTPNGL (SEQ ID NO: 6) is the subject of priming phosphorylation by the mitosis-promoting factor (CDK1/cyclin B). The phosphorylated motif LLCS[pT]PNGL (SEQ ID NO: 5) comprises the PBD interacting sequence of CDC25c thereby recruiting it as a PLK1 substrate.

The structure activity relationship analysis was undertaken through analog synthesis and computational design and utilization of a competitive fluorescence polarization (FP) binding assay using the flourescein labelled non-natural PBD sequence MAGPMQS[pT]PLNGAKK (SEQ ID NO: 7).

Since non-phosphothreonine containing peptides have been shown to bind to the PBD using isothermal titration calorimetry and X-ray crystallography, a number of peptide analogs of the native CDC25c sequence were synthesized. These included both natural and non-natural residues, exploring substitution of the terminus, e.g., the LLC (SEQ ID NO: 17) hydrophobic tripeptide motif on the N-terminus, and replacement of the phosphorylated threonine residue.

Examples of the peptide analogs examined and the measured $IC_{50}$ for each are shown in Table 1, below. No detectable binding was observed in the non-phosphorylated context for peptides incorporating various hydrophobic substitutions, despite previous observations that such peptides retain activity. This possibly reflects the use of different PBD domain proteins in prior studies, which include a shorter version produced for crystallography (residues 367-603) and a longer construct (326-663) used in binding studies. To probe this further, PBD sequences were examined for binding to both constructs. No evidence for affinity of non-phosphorylated peptides was detected despite robust binding of the native phospho-CDC25c sequence, LLCS[pT]PNGL (Table 1, sample no. 292, SEQ ID NO: 5). This discrepancy is believed to be a consequence of the competitive binding assay. It was observed, however, that phospho-CDC25c binds with significantly higher affinity for the shorter PBD construct (1.3 µM $IC_{50}$ for competition of fluorescent peptide binding to PLK1 326-603), which is believed to indicate that PLK1 subcellular localization functions are regulated through the multiple conformational states that have been previously described.

TABLE 1

| Sample No. | SEQ ID NO. | Sequence | PLK1 PBD $IC_{50}$ |
| --- | --- | --- | --- |
| 292 | SEQ ID NO: 5 | LLCS[pT]PNGL | 0.42 |
| 5821 | SEQ ID NO: 8 | Ac-LLCS[pT]PNGL | 0.5 |
| 345 | SEQ ID NO: 9 | LLCSEPNGL | 350 |
| 5795 | SEQ ID NO: 10 | LDCS[pT]PNGL | 3 |
| 5783 | SEQ ID NO: 11 | LLAAAPNGL | >600 |
| 5714 | SEQ ID NO: 12 | S[pT]PNGL | >600 |
| 5649 | SEQ ID NO: 4 | LHS[pT]AI | 200 |
| 5781 | SEQ ID NO: 13 | Ac-LHS[pT]AI | 5 |
| 5782 | SEQ ID NO: 14 | Ac-AHS[pT]AI | 15 |
| 5743 | SEQ ID NO: 15 | Ac-PLHS[pT]A | 2 |
| 5744 | SEQ ID NO: 16 | Ac-PLHSEA | 500 |

Synthesis and testing of a peptide library incorporating semi-conservative replacements and phosphothreonine isosteres revealed that only the glutamic acid containing sequence (Table 1, sample no. 345, SEQ ID NO: 9) possessed detectable binding to the PBD. While almost a thousand fold less potent, the carboxylate containing side chain nonetheless partially mimics the phosphate thereby suggesting useful structure activity relationship information that could be exploited in small molecule design. Additional peptide analogs were synthesized based upon the PBIP sequence and where the N-terminal end was truncated and modified by replacing Leu-Leu-Cys (SEQ ID NO: 17) with Leu-His (SEQ ID NO: 18) (LHS[pT]PNGL, SEQ ID NO: 26) and where the residues C-terminal to the pThr (Pro-Asn-Gly-Leu) (SEQ ID NO: 19) were replaced with Ala-Ile (SEQ ID NO: 20) (LLCS[pT]AI, SEQ ID NO: 23). A serendipitous discovery resulted from generating peptides without the N-terminal acetyl group previously incorporated in PBD inhibitory peptides. Interestingly, the des-acetyl peptide exhibited dramatically reduced potency relative to the expected value (Table 1, sample no. 5649, SEQ ID NO: 4). After resynthesis and appending of the acetyl group to the N-terminus, the potency of the native sequence was found to be similar to the reported compound (Table 1, sample no. 5781, SEQ ID NO: 13)). The acetylated peptide ($IC_{50}$ of 5 µM) is 40 fold more potent than the non-acetylated version ($IC_{50}$ of 200 µM) and is just six-fold less potent than the parent peptide containing the N-terminal LLC (SEQ ID NO: 17). The essential contribution of this acetyl group to binding was not previously apparent despite evidence of H-bonding in crystal structures of Ac-LHS[pT]AI (sample no. 5781, SEQ ID NO: 13) in complex with the PBD. The decreased potency of the non-actetylated peptide therefore suggests that the H-bond from the carbonyl of the acetyl group to the guanidinum side chain of Arg516 is a critical determinant for binding to the PBD since no interactions of the amide nitrogen or methyl group are observed. Partial contribution to the potency increase derives from the fact that repulsion of the positively charged N-terminal amino group with the basic side chain of Arg516 is mitigated in the acetylated compound.

Further to this observation, other acetylated sequences were generated and tested in the PBD binding assay in order to probe the structure activity relationship of the truncated molecules. In order to test the contributions of the Leu side chain in this context, Ac-AHS[pT]AI (sample no. 5782, SEQ ID NO: 14) was synthesized. As observed from the available crystal structures (sample no. 5781, SEQ ID NO: 13), the branched aliphatic side chain has no significant non-bonded interactions with the PBD groove suggesting that the alanine replacement should display similar potency. After testing, the resulting $IC_{50}$ was 3 fold higher (Table 1, sample no. 5782, SEQ ID NO: 14), which indicates that the side chain contributes entropically to peptide binding through conformational effects.

An acetylated peptide, truncated at the C-terminus with respect to the native CDC25c sequence, Ac-PLHS[pT]A (sample no. 5743, SEQ ID NO: 15) (Pro-Leu-His replacing Leu-Leu-Cys (SEQ ID NO: 17)), was synthesized, tested in the FP assay and shown to have comparable activity to Ac-LHs[pT]AI (Table 1, compare sample no. 5743 (SEQ ID NO: 15) to sample no. 5781 (SEQ ID NO: 13)). This observation suggests that the N-terminal proline compensates for removal of the C-terminal isoleucine and the relative affinities are consistent with the results previously obtained for these compounds. Sample no. 5743 (SEQ ID NO: 15) also reveals that high affinity and PLK1 selective binding can be obtained through interaction of the PBD subsite occupied by the N-terminal tripeptide of CDC25c. A glutamic acid was also substituted for phosphothreonine in the PBIP sequence (sample no. 5744, SEQ ID NO: 16). In agreement with results seen for the glutamic acid substitution in the peptide CDC25c context (sample no. 345, SEQ ID NO: 9), sample no. 5744 (SEQ ID NO: 16) weakly but detectably bound to the PBD (Table 1), again suggesting that the carboxylate containing side chain partially mimics the phosphate and can be exploited in design of a non-peptide replacement segment. In order to assess the contribution of the N-terminal tripeptide to binding of the CDC25c native sequence, the peptide S[pT]PNGL (sample no. 5714, SEQ ID NO:12) was synthesized. In vitro testing in the FP assay confirmed the critical interactions of the LLC (SEQ ID NO: 17) trimer as no detectable binding was observed for the truncated peptide. The peptide sequence LLAAAPNGL (sample no. 5783, SEQ ID NO:11) was included as a negative control in which three residues were mutated to alanines in order to completely abrogate binding.

The structure activity relationship information generated through study of the binding of peptides to the PBD provides key insights into the design and synthesis of the more drug-like inhibitors described herein as may be useful for development as anti-tumor therapeutics. For example, these insights suggest that focusing on the PBD subsite occupied by the LLC (SEQ ID NO: 17) tripeptide in conjunction with the incorporation of phosphothreonine mimetics should yield non-peptides with sufficient potency.

Example 2

1800 carboxylate containing fragments were examined using LigandFit for docking into the volume of the peptide binding groove occupied by the LLC (SEQ ID NO: 17) tripeptide of the inhibitor LLCS[pT]PNGL (SEQ ID NO: 5).

Since S[pT]PNGL (sample no. 5714, SEQ ID NO: 12, Table 1) possesses no measurable affinity for PBD, capped peptides were considered hits if they had measurable binding in an FP assay. Based on predictions of high scoring fragment alternatives for the tripeptide, 34 fragment ligated inhibitors were synthesized.

After initial screening and dose-response testing in an FP assay, 7 fragment ligated inhibitory proteins were identified as having measurable activity (IC$_{50}$ values ranging between 200 and 400 µM. A further 5 fragment ligated inhibitory proteins were formed and identified as having an IC$_{50}$ between 400 and 600 µM. Table 2, below, presents these 12 samples as well as second and third generation fragment ligated inhibitors and results of the FP assays for each.

TABLE 2

| Sample No. | Compound Abbbreviation of fragment name | Ligated Fragment | IC50 | Apoptosis @ 24 hr, 30 mM | Aberrant mitoses @ 24 hr, 30 mM |
|---|---|---|---|---|---|
| 5591 | — | | 375 | ND | ND |
| 5593 | — | | 380 | ND | ND |
| 5594 | 1G1-S[pT]PNGL (SEQ ID NO: 12) | | 350 | ND | ND |
| 5595 | — | | 475 | ND | ND |
| 5597 | — | | 500 | ND | ND |

TABLE 2-continued
| Sample No. | Compound Abbbreviation of fragment name | Ligated Fragment | IC50 | Apoptosis @ 24 hr, 30 mM | Aberrant mitoses @ 24 hr, 30 mM |
|---|---|---|---|---|---|
| 5598 | 1G2-S[pT]PNGL (SEQ ID NO: 12) | 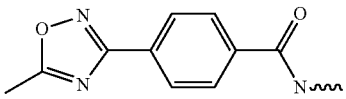 | 320 | ND | ND |
| 5599 | — | 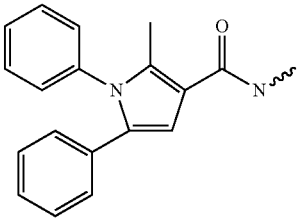 | 600 | ND | ND |
| 5600 | — | 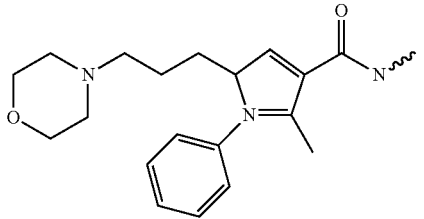 | 550 | ND | ND |
| 5601 | — | 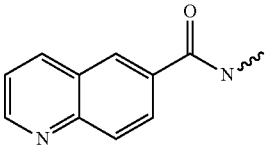 | 400 | ND | ND |
| 5603 | 1G3-S[pT]PNGL (SEQ ID NO: 12) | 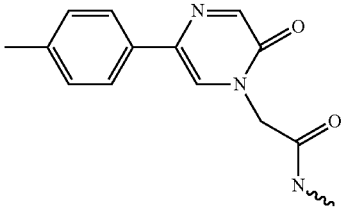 | 250 | ND | ND |
| 5604 | — | 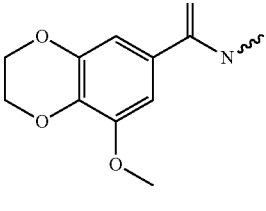 | 300 | ND | ND |
| 5607 | — | 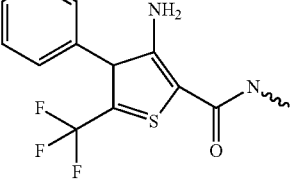 | >600 | ND | ND |

TABLE 2-continued

| Sample No. | Compound Abbbreviation of fragment name | Ligated Fragment | IC50 | Apoptosis @ 24 hr, 30 mM | Aberrant mitoses @ 24 hr, 30 mM |
|---|---|---|---|---|---|
| 5723 | — | naphthalene-1-carboxamide | 104 | ND | ND |
| 5754 | 4-methoxybenzoic acid | 4-methoxybenzamide | 125 | ND | ND |
| 5756 | 2G1-S[pT]PBGL (SEQ ID NO: 12) | 4-methoxynaphthalene-1-carboxamide | 99 | ND | ND |
| 5785 | 4-prpoxybenzoic acid | 4-propoxybenzamide | 29.5 | ND | ND |
| 5786 | 4-ethoxybenzoic acid | 4-ethoxybenzamide | 64.7 | ND | ND |
| 5788 | 3G1-S[pT]PNGL (4-ethylbenzoic acid) (SEQ ID NO: 21) | 4-ethylbenzamide | 16.5 | 36.2% | 47.9% |
| 5791 | 4-(Methylthio) benzoic acid | 4-(methylthio)benzamide | 18.5 | ND | ND |
| 5792 | 4-(Methylamino) benzoic acid | 4-(methylamino)benzamide | 31.2 | ND | ND |
| 5826 | 4-propylbenzoic acid | 4-propylbenzamide | 10.8 | ND | ND |
| 5827 | 3G2-S[pT]PNGL (4-butylbenzoic acid) (SEQ ID NO: 22) | 4-butylbenzamide | 8.6 | 55.5% | 53.8% |

TABLE 2-continued

| Sample No. | Compound Abbbreviation of fragment name | Ligated Fragment | IC50 | Apoptosis @ 24 hr, 30 mM | Aberrant mitoses @ 24 hr, 30 mM |
|---|---|---|---|---|---|
| 5830 | 4-(Propylamino) benzoic acid | [structure] | 16.5 | ND | ND |
| 5743 | Ac-PLHS[pT]A (SEQ ID NO: 15) | — | 2 | 34.0% | 40.3% |

Figure 1B:
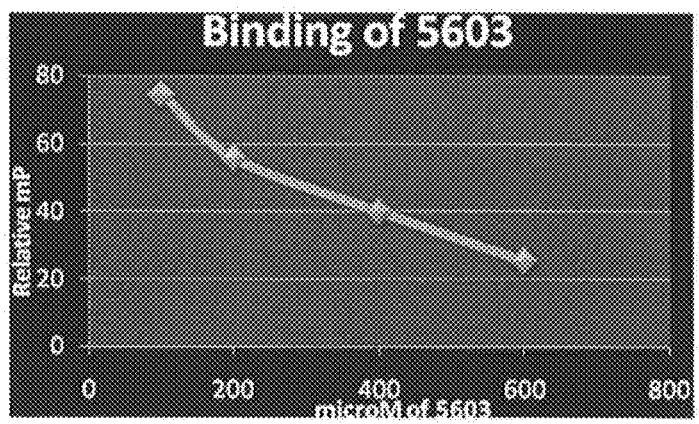

Data obtained from the FP assays were utilized to produce binding curves for the fragment ligated inhibitors. FIG. 1A and FIG. 1B illustrate the binding curves obtained for sample no. 5594 and sample no. 5603, respectively.

Figure 2:
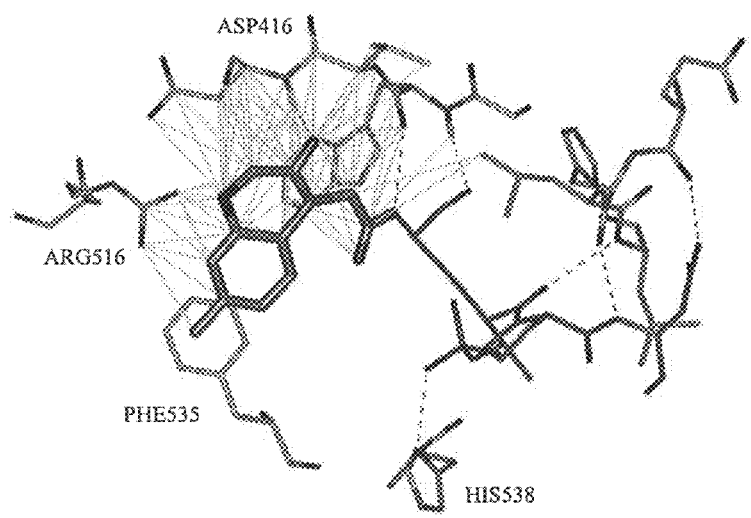
FIG. 2 is a schematic illustration of a non-peptide fragment developed as described herein and the predicted interaction of the non-peptide fragment with a PBD subpocket of a PLK1 protein.

Results indicated a total hit rate of 30% and thereby confirmed the success of the strategy in the initial application to the PBD. While initial fragment ligated inhibitors were of considerably lower potency than the native CDC25c sequence, an increase relative to the truncated molecule (S[pT]PNGL, Sample No. 5714, SEQ ID NO: 12) was apparent. The most potent fragments observed in the first generation were a benzo[1,4]oxazin-3-one pharmacophore and a similar 5-phenylpyrazinone core (Table 2, 1G1 and 1G2). Based on the assumption that interactions of the predicted docked fragment structure and the truncated peptide will be preserved in the fragment ligated inhibitor, it is a relatively straightforward process to obtain a protein-ligand complex for the fragment ligated inhibitor through molecular modeling. Using this approach, it was observed that the pyrazinone carbonyl donates an H-bond to the backbone amide nitrogen of Asp416 while the rings make numerous van der Waals contacts with the residues contacting the tripeptide in the PBD sub-pocket including Trp414 and Phe535 (FIG. 2). The peptide structure activity relationship obtained in Example 1 suggests that appropriate modification of the 5-phenyl group with the H-bond acceptors should lead to improvements in binding on order of the increases observed with addition of the acetyl group to LHS[pT]AI (Sample No. 5781, SEQ ID NO: 13).

As follow up to the initial hits, incorporation of appropriately substituted naphthoic and benzoic acid derivatives onto the N-terminus of the hexapeptide were carried out to take advantage of features of the PBD groove. Second generation derivatives were predicted to be more simple pharmacophores of the initial hits and were obtained and incorporated as fragment groups through synthesis of fragment ligated inhibitor molecules (Table 2, 2G1, sample no. 5756). After in vitro testing of second generation the formed fragment ligated inhibitors, potency enhancements were observed relative to the initial hits. The best of these compounds, 3G1-S[pT]PNGL (4-ethylbenzoic acid) (Table 2, sample no. 5788, SEQ ID NO: 21) had an $IC_{50}$ of 16.5 μM and therefore was quite successful in recapitulating the potency represented in the native CDC25c peptide. A significant aspect of the result obtained for sample no. 5788 was that the N-terminal tripeptide (Leu-Leu-Cys (SEQ ID NO: 17)) had been replaced with a fragment capping group approximately ⅓ the size of the native sequence. In addition, among several analogs obtained, it was apparent that these compounds exploit novel features of the PBD groove (unoccupied in other peptide structures) and that a clear structure-activity relationship was evident from the range of activities observed. Indeed, synthesis of third generation derivatives exploiting this novel interaction resulted in compound, 3G2-S[pT]PNGL (4-butylbenzoic acid) (Table 2, sample no. 5827, SEQ ID NO: 22) resulted in increased PBD affinity with an $IC_{50}$ of 8.6 μM obtained. As delineated through the peptide structure activity relationship information, the benzoic acid structure was found suitable for further derivatization and would allow for incorporation appropriate functionality to mimic the H-bond interactions of the acetyl group observed in the peptide context.

Three iterations of the disclosed process for developing a fragment ligated inhibitory protein enabled substitution of the Leu-Leu-Cys (SEQ ID NO: 17) tripeptide with derivatized benzoic acids approximately ⅓ the size, within one log of the activity of the endogenous CDC25c peptide and almost equivalent in potency to the truncated PBIP1 peptides (e.g., NCap-S[pT]AI (SEQ ID NO: 24). A clear structure-activity relationship was observed for this series, therefore providing a scaffold for further optimization. Plenty of scope exists for further derivatization of this core structure in order to exploit non-bonded interactions observed in the peptide crystal structures. Addition of H-bond acceptor groups to the $3^{rd}$ generation scaffold in order to mimic the contacts of the acetyl group in the PBIP peptides is believed to be a viable approach and should result in increased potency. Future iterations can exploit the structure activity relationship information that suggests that when synthesized in the C-terminally truncated contexts (i.e. NCap-S[pT]A, SEQ ID NO: 25), fragment ligated inhibitory proteins potencies will be similar.

Example 3

In order to uncover evidence of PLK1 targeting in living cells by the fragment ligated inhibitors, a series of studies were conducted using the more promising PBD inhibitory compounds identified by the in vitro binding assay described above. To date, a limited body of data is available on cellularly administered peptides due to their lack of permeability and stability. In order to overcome these disadvantages, the recently developed QQ reagent (see, e.g., Li, et al., Methods in Cell Biology, 2001. 90: p. 287-325) was utilized to successfully transfect peptides into cells. To demonstrate successful transfection, HeLa cells were treated with the QQ modified, native CDC25c phosphopeptide with an N-terminal fluorescein label. Extensive green fluorescence was observed in the cell interior with concentrated intensity indicated nuclear localization of the peptide.

Figure 3:
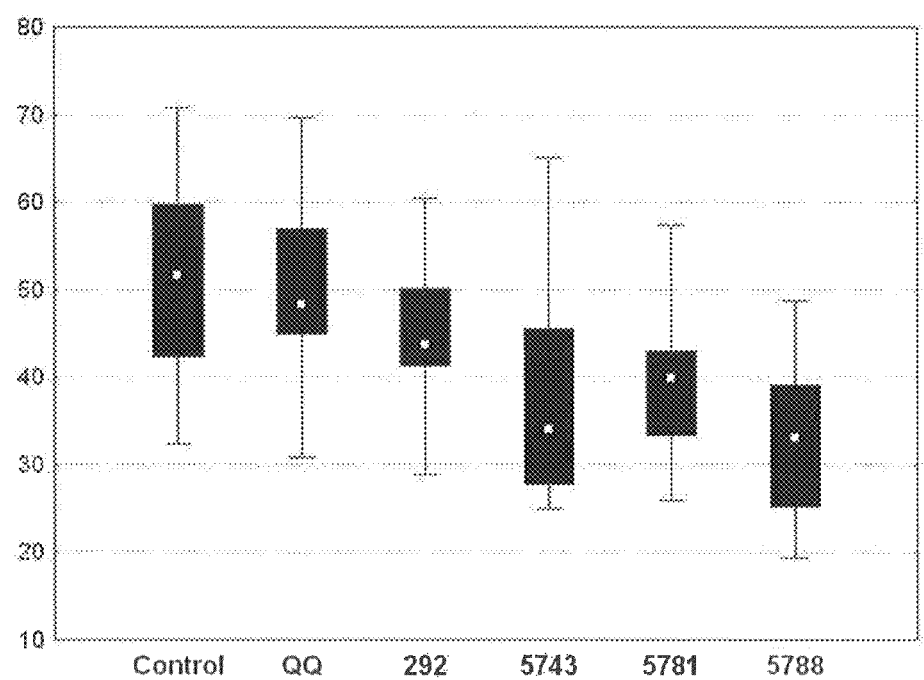
FIG. 3 graphically presents the relative fluorescence intensity of PLK1 at the centrosome following incubation with a control, a peptide PLK1 inhibitor selective for the PBD domain, or a fragment ligated inhibitor formed as described herein.

Normally, PLK1 is recruited to the centrosomes and kinetochores, but interference with this step and its catalytic activity causes improper centrosome duplication and spindle defects. To determine if QQ transfected peptides were able to generate phenotypes consistent with blocking of recruitment through the PBD, localization of PLK1 at the centrosomes in metaphase cells was visualized and quantified through immunofluorescence in HeLa cells expressing GFP fused to Histone H2B (also used to visualize chromosomes during mitosis). The average relative fluorescence intensity of PLK1 at the centrosome was 51.2 and 49.2 (arbitrary fluorescence units) for the PBS treated control and QQ controls respectively (FIG. 3). Three peptides and one fragment ligated inhibitor were tested for their ability to interfere with PLK1 centrosomal localization. These included the CDC25c parent peptide LLCS[pT]PNGL (sample no, 292, SEQ ID NO: 5), two truncated and acetylated peptides, Ac-PLHS[pT]A (sample no. 5743, SEQ ID NO: 15) and Ac-LHS[pT]AI (sample no. 5781, SEQ ID NO: 13) and one of the most promising fragment ligated inhibitors described above, 3G1-S[pT]PNGL (4-ethylbenzoic acid) (sample no. 5788, SEQ ID NO: 21). Treatment with the acetylated peptides sample no. 5743 (SEQ ID NO: 15) and sample no. 5781 (SEQ ID NO: 13) (30 µM) reduced the relative fluorescence intensity of PLK1 staining at centrosomes to 33 and 35, respectively, while treatment with sample no. 5788 (SEQ ID NO: 21) resulted in even more marked effects (32 at 10 µM) suggesting that the peptides and fragment ligated inhibitor sample no. 5788 were specifically targeting PLK1 (FIG. 3). Treatment with sample no. 292 (SEQ ID NO: 5) only slightly reduced the fluorescent intensity to 45, which was not a statistically significant difference. Although sample no. 292 (SEQ ID NO: 5) provided the lowest $IC_{50}$ value in the in vitro binding assay, the reduced potency is not surprising given the poor pharmaceutical properties of unmodified peptides in cells.

In addition to the direct reduction in PLK1 localization observed, cells were examined for mitotic phenotypes consistent with PLK1 inhibitory effects following treatment with the PBD inhibitors. Two such phenotypes include a prometaphase/metaphase arrest, and the observation of monopolar or multipolar spindles in metaphase. The GFP-H2B HeLa cells were utilized to visualize chromosomes during mitosis after treatment with PBD inhibitors transfected using QQ reagent. Prometaphase/metaphase cells were scored as abnormal if the number of PLK1-stained centrosomes did not equal 2 or if there was an improper chromosome alignment.

Figure 4:
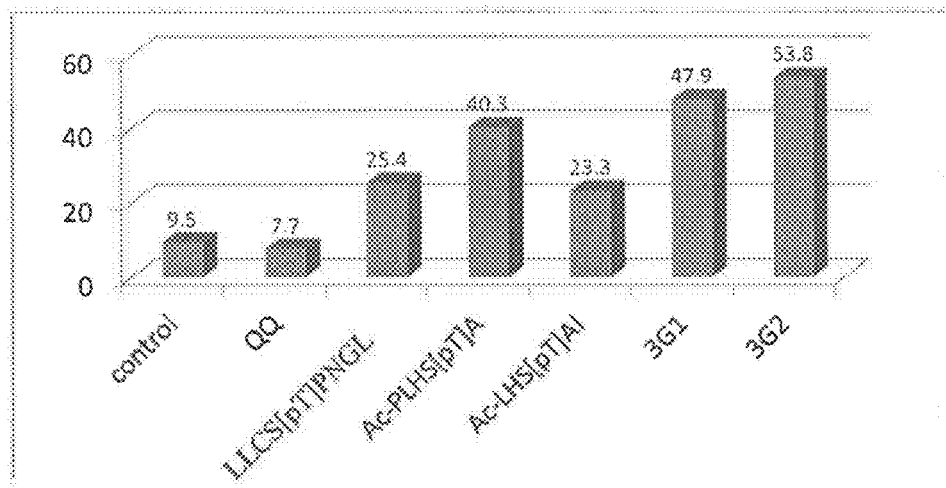
FIG. 4 graphically presents the percentage of aberrant prometaphase/metaphase features of cells transfected with a control, a peptide PLK1 inhibitor selective for the PBD domain, or a fragment ligated inhibitor formed as described herein.

The large majority of mitotic cells mock or QQ-alone treated were observed to be in normal prometaphase or metaphase (<10% of the cells were scored as aberrant, FIG. 3). Treatment of cells with the triple alanine negative control peptide (sample no. 5783) and the parent CDC25c sequence (sample no. 292, SEQ ID NO: 5) resulted in 9.5% and 25% aberrant prometaphase/metaphase features following a 30 µM dose (FIG. 3) respectively. Sample no. 5743 (Ac-PLHS [pT]A) (SEQ ID NO: 15) resulted in a more potent and dose dependent induction of cells with aberrant prometaphase or metaphase since at a 10 µM dose, 32% of the cells showed mitotic abnormalities and at 30 µM, the fraction of aberrant cells rose to 40.3% (FIG. 4). Treatment with sample no, 5781 (SEQ ID NO: 13), a weaker in vitro PBD inhibitor resulted in a less pronounced cellular effect with approximately 23% demonstrating aberrant metaphase at a dose of 30 µM. Interestingly, of all the peptidic compounds tested, the fragment ligated inhibitors, namely 3G1-S[pT]PNGL (4-ethylbenzoic acid) (sample no. 5788, SEQ ID NO: 21) and 3G2-S[pT]PNGL (4-butylbenzoic acid) (sample no. 5827, SEQ ID NO: 22), led to the most pronounced effects in the induction of aberrant mitosis, with values of 48 and 54% respectively at 30 µM.

Figure 5:
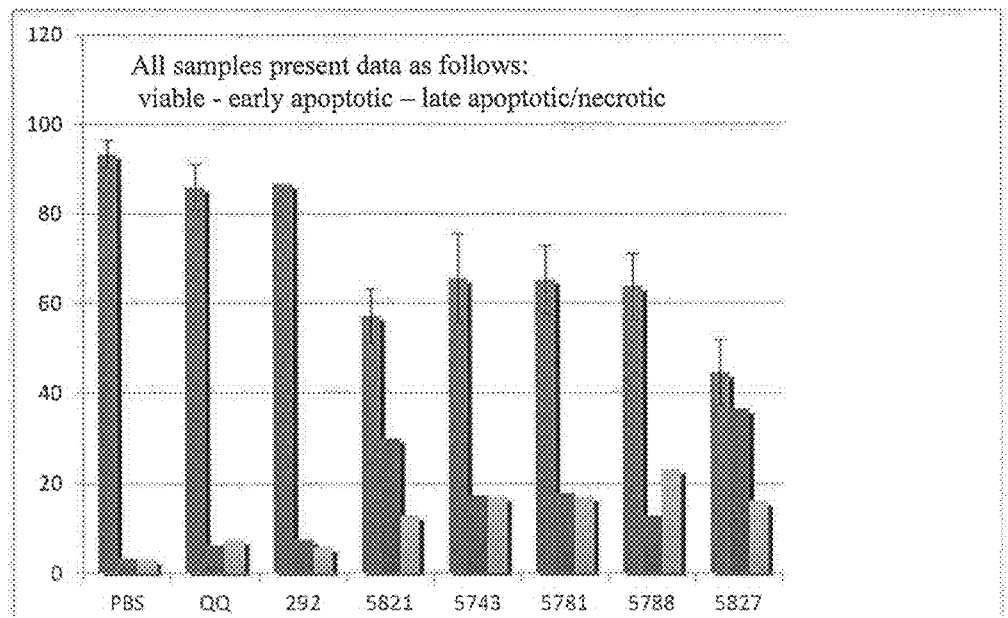
FIG. 5 graphically presents the results of an apoptosis/necrosis assay used to measure cell death induced in cells transfected with a control, a peptide PLK1 inhibitor selective for the PBD domain, or a fragment ligated inhibitor formed as described herein.

An Annexin V (AV)-Propidium Iodide (PI) apoptosis/ necrosis assay was used to measure cell death induced by the PBD inhibitors. Using flow cytometry, cells were scored as viable, early apoptotic and late apoptotic/necrotic. The mock and QQ treatments did not significantly induce cell death although a slight increase in apoptosis was observed with QQ alone. HeLa cells were transfected with sample nos. 292 (SEQ ID NO: 5), 5821 (SEQ ID NO: 8), 5743 (SEQ ID NO: 15) and 5781 (SEQ ID NO: 13) at a 30 µM dose. Both 6-mer peptides sample no. (5743 SEQ ID NO: 15) and sample no. 5781 (SEQ ID NO: 13) behaved similarly after 24 hours post-treatment with the percentage of viable cells decreasing by 30% and similar levels of early and late apoptosis with each transfected inhibitor (FIG. 5). Interestingly, the most potent PBD inhibitory peptide sample no. 292 (SEQ ID NO: 5), when transfected did not induce significant levels of apoptosis relative to the controls. An acetylated version of this compound, however, was more potent despite having a similar $IC_{50}$ in the FP assay. After 24 hours, it reduced the fraction of viable cells to 57% therefore indicating a stabilizing effect of the acetyl group on its cellular activity. Treatment of HeLa cells with the two PBD fragment ligated inhibitors, sample no. 5788 (3G1, SEQ ID NO: 21) and sample no. 5827 (3G2, SEQ ID NO: 22) resulted in the most profound effects in apoptotic induction at the 30 µM dose. Relative to the peptide inhibitors and despite having weaker affinity, these two compounds had the lowest proportion of viable cells with 64 and 45% respectively after 24 hours. In particular, the most potent fragment ligated inhibitor in the in vitro assay, sample no. 5827 (3G2, SEQ ID NO: 22), had a similar proportion of viable and early apoptotic cells and increased fraction of late apoptotic cells relative to the weaker binding compound. These results suggest that the capping group provides protection from cellular degradation of the peptides and the longer half life results in increased cellular potency. Taken together, these results confirm that PBD inhibitors induced significant levels of cell death through apoptosis and the two most potent fragment ligated inhibitors described herein are the most effective in this cellular assay.

These examples demonstrate that PBD fragment ligated inhibitors are indeed directly interfering with the functions of PLK1. Specifically, treatment resulted in reduced PLK1 localization to centrosomes, aberrant mitoses as visualized by mono and multipolar spindles, abnormal chromosome alignment during metaphase, and cell death through apoptosis. Consistent data from each cellular endpoint for the $3^{rd}$ generation fragment ligated inhibitors suggests that despite weaker in vitro binding, the small-molecule-peptide hybrids have increased cellular activity relative to the peptidic inhibitors. Addition of the N-terminal capping group will stabilize these compounds against cellular proteolysis, therefore improving their drug-likeness.

Results with peptidic inhibitors and fragment ligated inhibitor PBD in this study clearly demonstrate that a phenotype more consistent with blocking the enzymatic and localization functions of PLK1 is obtained with the disclosed materials. This implies that small molecule inhibitors such as PPG and Poloxin, while interesting biological probes, do not recapitulate a complete PLK1 phenotype and therefore may not possess a desirable level of anti-tumor activity.

It will be appreciated that the foregoing examples, given for purposes of illustration, are not to be construed as limiting the scope of this disclosure. Although only a few exemplary embodiments have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A fragment ligated inhibitor that is selective to a polo box domain of a PLK1 protein, the fragment ligated inhibitor comprising a peptide fragment and a non-peptide fragment, the peptide fragment comprising S[pT]PNGL (SEQ ID NO: 12), LLCS[pT]AI (SEQ ID NO: 23), S[pT]AI (SEQ ID NO: 24) or S[pT]A (SEQ ID NO: 25), the peptide fragment including no additional peptide residues on the N-terminus of the peptide fragment, the non-peptide fragment comprising a 4-alkyl benzoic acid, a 4-alkylthio benzoic acid, a 4-alkylamino benzoic acid, or a 4-alkoxy benzoic acid, wherein the non-peptide fragment is directly bonded to the N-terminus of the peptide fragment.

2. The fragment ligated inhibitor according to claim 1, wherein the non-peptide fragment comprises an unsubstituted alkyl group.

3. The fragment ligated inhibitor according to claim 2, wherein the non-peptide fragment comprises an unsubstituted straight chain alkyl group.

4. The fragment ligated inhibitor according to claim 1, wherein the non-peptide fragment comprises ethyl-benzoic acid, propyl benzoic acid, or butyl-benzoic acid.

5. The fragment ligated inhibitor according to claim 1, wherein the non-peptide fragment comprises propylamino benzoic acid, methylamino benzoic acid, methylthio benzoic acid, ethyoxy benzoic acid, or propoxy benzoic acid.

* * * * *

```
                        SEQUENCE LISTING

<160> NUMBER OF SEQ ID NOS: 26

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: pThr or pSer
<220> FEATURE:
<221> NAME/KEY: MOD_RES
<222> LOCATION: (3)..(3)
<223> OTHER INFORMATION: Any amino acid preferably Pro

<400> SEQUENCE: 1

Ser Xaa Xaa
1

<210> SEQ ID NO 2
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: pThr

<400> SEQUENCE: 2

Ser Thr Pro
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: pThr

<400> SEQUENCE: 3

Pro Leu His Ser Thr
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (4)..(4)
<223> OTHER INFORMATION: pThr

<400> SEQUENCE: 4

Leu His Ser Thr Ala Ile
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: pThr

<400> SEQUENCE: 5

Leu Leu Cys Ser Thr Pro Asn Gly Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Leu Cys Ser Thr Pro Asn Gly Leu
1               5

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: pThr

<400> SEQUENCE: 7

Met Ala Gly Pro Met Gln Ser Thr Pro Leu Asn Gly Ala Lys Lys
1               5                   10                  15

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: pThr

<400> SEQUENCE: 8

Leu Leu Cys Ser Thr Pro Asn Gly Leu
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Leu Cys Ser Glu Pro Asn Gly Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: pThr

<400> SEQUENCE: 10

Leu Asp Cys Ser Thr Pro Asn Gly Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Leu Ala Ala Ala Pro Asn Gly Leu
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: pThr

<400> SEQUENCE: 12

Ser Thr Pro Asn Gly Leu
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: pThr
```

```
<400> SEQUENCE: 13

Leu His Ser Thr Ala Ile
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: pThr

<400> SEQUENCE: 14

Ala His Ser Thr Ala Ile
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (5)..(5)
<223> OTHER INFORMATION: pThr

<400> SEQUENCE: 15

Pro Leu His Ser Thr Ala
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac

<400> SEQUENCE: 16

Pro Leu His Ser Glu Ala
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Leu Cys
1

<210> SEQ ID NO 18
<211> LENGTH: 2
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 18

Leu His
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Asn Gly Leu
1

<210> SEQ ID NO 20
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Ile
1

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: pThr
<220> FEATURE:
<221> NAME/KEY: MOD_RES
<222> LOCATION: (6)..(6)
<223> OTHER INFORMATION: Leu-(4-ethylbenzoic acid)

<400> SEQUENCE: 21

Ser Thr Pro Asn Gly Leu
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: pThr
<220> FEATURE:
<221> NAME/KEY: MOD_RES
<222> LOCATION: (6)..(6)
<223> OTHER INFORMATION: Leu-(4-butylbenzoic acid)

<400> SEQUENCE: 22
```

Ser Thr Pro Asn Gly Leu
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: pThr

<400> SEQUENCE: 23

Leu Leu Cys Ser Thr Ala Ile
1               5

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: pThr

<400> SEQUENCE: 24

Ser Thr Ala Ile
1

<210> SEQ ID NO 25
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: pThr

<400> SEQUENCE: 25

Ser Thr Ala
1

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: pThr

<400> SEQUENCE: 26

Leu His Ser Thr Pro Asn Gly Leu
1               5